(12) United States Patent
Babinski et al.

(10) Patent No.: US 6,762,157 B1
(45) Date of Patent: Jul. 13, 2004

(54) LOW RESIDUE SURFACE TREATMENT

(75) Inventors: Linda J. Babinski, Kenosha, WI (US); Karen K. Kristopeit, Kenosha, WI (US); Francis J. Randall, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/629,368

(22) Filed: Jul. 31, 2000

(51) Int. Cl.⁷ .................................................. C11D 3/50
(52) U.S. Cl. ...................... 510/101; 510/289; 510/506; 510/518; 510/524; 510/535
(58) Field of Search ................................ 510/101, 289, 510/506, 518, 524, 535

(56) References Cited

U.S. PATENT DOCUMENTS

| | | | |
|---|---|---|---|
| 4,226,889 A | * 10/1980 | Yuhas | 424/59 |
| 5,578,563 A | 11/1996 | Trinh et al. | 510/513 |
| 5,663,134 A | 9/1997 | Trinh et al. | 510/406 |
| 5,670,475 A | 9/1997 | Trinh et al. | 510/470 |
| 5,783,544 A | 7/1998 | Trinh et al. | 510/293 |
| 5,939,060 A | 8/1999 | Trinh et al. | 424/76.4 |
| 5,968,404 A | 10/1999 | Trinh et al. | 252/8.91 |
| 6,077,318 A | 6/2000 | Trinh et al. | 8/137 |

FOREIGN PATENT DOCUMENTS

| | | | | |
|---|---|---|---|---|
| WO | WO 96/0440 A1 | 2/1996 | | |
| WO | WO 96/04938 | 2/1996 | | |
| WO | WO-98/56337 | * 12/1998 | ............ | C11D/3/50 |

* cited by examiner

*Primary Examiner*—Brian P. Mruk
*Assistant Examiner*—Eisa Elhilo

(57) ABSTRACT

An aqueous composition for the reduction or elimination of unpleasant odors from surfaces containing such odors comprises a perfume, a surfactant/solubilizer, a solvent/drying aid, an odor absorber, and, preferably, a buffer to maintain the desired pH. The solution contains minimal or no volatile organic compounds. Due to the specific nature of the combination of the surfactant/solubilizer and the solvent/drying aid, the use of fragrances previously too hydrophobic for use in an aqueous solution is possible, providing a large variety of efficient odor counteractants not previously available. The composition may optionally comprise additional components, such as preservatives, antimicrobials, anti-static compositions, anti-wrinkling agents, insect control agents, moth repellents, UV protectants, water-proofing agents, and textile treatment agents. The aqueous solution may be applied to a variety of surfaces, in sufficient quantity to wet the surface, preferably by spraying.

17 Claims, No Drawings

LOW RESIDUE SURFACE TREATMENT

RELATED APPLICATION(S)

Not applicable.

FEDERALLY SPONSORED RESEARCH OR DEVELOPMENT

Not applicable.

TECHNICAL FIELD

The present invention relates to aqueous compositions for reduction of objectionable odors from surfaces, comprising water, an odor absorber or odor in counteractant, perfume, solvent, solubilizer, and drying aid. The composition is designed to reduce the presence of objectionable odors, such as food odors, tobacco odors, perspiration, etc., on surfaces such as clothing or fabric such as on furniture. The compositions of the present invention are fast drying, and leave little or no residue on the surface after drying. While specifically designed for use with soft surfaces, such as fabrics, the compositions of the present invention may also be used on hard surfaces, such as garbage and refuse containers and recycling bins, or on such surfaces as appliances, counters, floors, cabinets, walls, and plumbing fixtures in kitchens and bath rooms.

BACKGROUND OF THE INVENTION

The present invention relates to an aqueous composition suitable for use as a freshening composition. Such a composition may be sprayed onto fabrics, particularly clothing, to restore the freshness thereof by elimination or reduction of malodors, between washings or dry cleanings. The composition may also be sprayed upon fabric covered furniture, or other surfaces, to eliminate malodors, such as pet odors, or tobacco odor, without deposition of a residue upon the surface.

A wide variety of deodorizing compositions are known, most commonly containing a perfume to mask or hide the malodor. Odor masking is the intentional concealment of one odor by over-powering it with another, preferably more acceptable odor, such as a fragrance. The masking perfumes used vary greatly, dependent upon application, such as masking perspiration odor, bathroom odor, pet odors, tobacco, etc. The appropriate fragrance for a given composition needs to be selected in accordance with the end product usage, as well as the goal to give the impression of freshness.

Odor modification, i.e. changing the odor by chemical modification, has also been used. Such techniques include oxidative degradation, which uses oxidizing agents such as oxygen bleaches, chlorine, sodium hypochlorite, or similar materials. In addition, reductive degradation has been attempted, using reducing agents such as sodium bisulfite to reduce malodor. However, both of these techniques are unacceptable due to damage they cause to fabrics, especially colored fabrics.

Other odor control methods employ actives which react with malodors having specific functional groups, such as biguanide polymers, which complex with organically bound nitrogen and/or sulfur atoms, or fatty alcohol esters of methyl methacrylic acid, which react with thiols, amine, and aldehydes. Such reactive materials, however, are generally not water soluble.

In addition, antibacterial and antifungal agents which regulate the odor producing microorganisms found on surfaces, have been employed, but are ineffective on malodors not caused by bacterial sources.

The present invention is most specifically directed at environmental odors, such as tobacco odor, cooking and food odors, and body odor. These odors are generally organic in nature, and frequently result from low molecular weight, straight-chain, branched, and unsaturated $C_6$–$C_{11}$ fatty acids.

U.S. Pat. No. 5,670,475, of Trinh et al is one of a number of patents related to the concept of reducing "malodor impression" from surfaces. Other relevant Trinh et al patents include U.S. Pat. Nos. 5,578,563; 5,633,134; 5,783,544; 5,968,404; 5,939,060; and 6,077,318. U.S. Pat. No. 5,670,475 teaches aqueous deodorizing compositions comprising up to about 1% perfume, and preferably including water-soluble cyclodextrins, water-soluble metal salts, and solubilizing aids. Cyclodextrins function in a manner similar to molecular sieves, which are also employed to entrap perfumes, odors, etc., and which may also be employed for removal of malodor from surfaces. Exemplary metal salts include zinc salts such as zinc sulfate, and exemplary solubilizers include ethoxylated aliphatic alcohols. In the preferred embodiments of the patent, the perfumes used in the compositions are those having a C log P of less than 3, it being indicated that such perfumes may be solubilized in water without the use of a solubilizing alcohol, whereas those perfumes with a C log P value greater than about 3 are less useful due to greater hydrophobicity. The patentee indicates that the composition contains less than about 5% low molecular weight monohydric alcohol. Cyclodextrin molecules are known to form complexes with perfume ingredients, and have been used as perfume carriers in the past. Trinh et al teach that fabrics treated with cyclodextrin exhibit perfume release upon rewetting, resulting in an impression of freshness of the fabric when said fabric is rewetted.

However, the prior art compositions are subject to slow rates of drying, and deposition of residues on the substrates treated. It is also to be noted that the Trinh et al reference specifically suggests that the perfumes used be those having a C log P value of 3 or less, to require the use of predominant proportions of those perfumes which are most hydrophilic or water soluble. This limitation prevents the utilization of a large number of popular and effective scents useful for the purpose of reducing malodor impression.

However, it is also to be noted that the presence of volatile organic compounds, or VOCs, such as alcohols, is not desirable, even though they are very effective solubilizers for perfumes, and impart rapid dry time to a surface treatment system. Such solvents are often odor objectionable in themselves, as well as being environmentally undesirable. Accordingly, it is an object of the present invention to provide a water-based deodorizing composition for treatment of surfaces, said composition preferably not containing objectionable VOCs, while still permitting the use of hydrophobic fragrances.

SUMMARY OF THE INVENTION

In one aspect, the invention is directed to a water-based deodorizing composition for the treatment of surfaces, the composition having a good dry time without use of volatile ingredients such as alcohols, and leaving little or no residue on the surface treated. The invention also relates to methods for using this composition for deodorizing surfaces such as fabrics and clothing.

In yet another form, the invention provides a low residue treatment for the removal of odors on surfaces, using a composition containing fragrances with a C log P value greater than about 3. The composition of the present invention further removes odors without damage to surfaces, and has an acceptable dry time without the addition of VOCs.

The compositions of this invention may be applied to any surface which would not be damaged, objectionably spotted, or otherwise compromised by the application of an aqueous spray, if that surface is subject to malodor retention. For example, one would not spray a rice paper screen with an aqueous composition of the present invention, but one may use said composition on the surface of a cloth or wooden screen, or a leather or fabric car seat. The present compositions are not intended as cleansing agents, such as may be used to clean a hard surface such as a glass table, mirror, kitchen counter, toilet, or trash receptacle, but such compositions may be sprayed upon such surfaces if they have become odorous. In such cases, the surface should first be cleaned in a conventional manner, and then the composition should be sprayed upon the cleaned surface and allowed to dry without wiping, to minimize streaking or clouding of the surface, particularly of shiny surfaces, while providing maximum deodorizing effect. As indicated, the compositions of this invention are primarily intended for use on soft surfaces, such as clothing, shoes, carpeting, upholstery, curtains, draperies, linens, etc., but are not limited to such surfaces. These compositions, by virtue of the fact that they leave little or no residue upon drying, and are non-staining, non-toxic and non-injurious to most surfaces when used as intended, may be used upon almost any surface which may be contacted with an aqueous spray, such as kitchen and bath counters, appliances, and fixtures, floors, walls, and containers such as garbage cans, storage bins, etc., which are subject to malodor retention from materials with which they come in contact, or from air borne malodors such as smoke and tobacco odors.

Preferred embodiments of the invention contain a solvent to surfactant ratio of approximately 2:1, and a fragrance to surfactant ratio of 1:3. The compositions taught also exhibit a preferred skin compatible pH range of from 5 to 6, although a pH range of from about 3 to about 7 is acceptable. More-over, the composition may be incorporated into a spray dispenser to create a consumer product which may be readily used in the home or elsewhere to reduce or eliminate objectionable odors upon a surface without leaving a stain or residue.

Thus, a primary object of the invention is to provide an aqueous composition which may be applied, preferably but not necessarily as a spray, to a surface to lessen or eliminate the presence of malodors in or on said surface. Another object is to provide a means for removal of objectionable odors from fabrics, such as clothing, without staining the fabric or leaving an objectionable residue thereupon, preferably without the use of compositions containing objectionable VOCs.

The objects of the present invention therefore include providing a fragranced is aqueous composition comprising, for example, a butyl ether solvent and drying aid, a primary alcohol ethoxylate solvent or solubilizer for the fragrance, a metal salt odor absorber, pH adjustment means, and a preservative.

These and still other objects and advantages of the present invention (e.g. methods for using such compositions) will be apparent from the description which follows, which description is merely of the preferred embodiments. Thus, the claims should be looked to in order to understand the full scope of the invention.

DETAILED DESCRIPTION OF THE INVENTION

Aqueous solutions of active ingredients are used in the present invention for the treatment of surfaces to eliminate or reduce odors. The preferred carrier is accordingly water, per se, which may be softened, distilled, deionized, or tap water, and which is relatively pure, containing no material which will leave a residue or stain upon surfaces, such as fabric, upon which the solution is sprayed and allowed to dry. The water also should preferably contain little or no low molecular weight alcohol, or other VOCs. Such materials may be present in limited amounts due to their presence in some perfumes, preservatives, and/or stabilizers, but it is preferred that the level of such VOCs be limited to less than about 1 percent, and preferably less than about 0.25 percent.

The present invention thus relates to an aqueous composition for reduction of objectionable odors from surfaces, said composition comprising water, odor absorber, fragrance, a surfactant/solubilizer, and a solvent/drying aid. More specifically, the composition comprises from about 0.01 to about 1.0 weight percent of a fragrance or perfume, said perfume being any perfume which exhibits water solubility sufficient, in the presence of a solubilizer therefor, for the purpose of the invention. Such perfumes are a matter of individual taste and preference, and may be varied to satisfy the preferences of differing markets internationally, or to complement or counter the specific malodor being attacked.

The perfumes suitable for use in the present invention are those which have odor characteristics acceptable for the purpose of reducing or eliminating the impression of unacceptable odors, primarily by masking such unacceptable odors. Whereas in the past, the fragrance materials used for such purpose were limited by their hydrophobic nature, applicant has now determined that many previously unsuitable fragrances may be used in the aqueous solutions of the present invention, but only if utilized with specific surfactant/solubilizers as set forth herein. For example, the perfumes suitable for use in the present invention include such perfumes as are commonly referred to as fresh clean, spicy, floral, citrus, ozone, and marine types. Preferred perfumes are selected from those referred to as fresh clean, and floral types. Preferably, the treatment solution of the present invention contains an effective amount of perfume to provide a freshening fragrance to surfaces upon first application, and some lingering fragrance during wear, and after drying to the touch. Effective levels of perfume are from about 0.01 percent to about 1.0 percent, preferably from about 0.01 percent to about 0.5 percent, and most preferably from about 0.015 percent to about 0.3 percent by weight.

To achieve the utilization of many more desirable fragrances in the present invention, it is necessary to provide for their solubilization in the water base of the composition. It has now been found that fragrances with a C log P value of greater than 3 may be utilized in the present invention, whereas previous attempts to utilize such fragrances have been unsuccessful. The term C log P as used herein refers to the degree of hydrophobicity of a perfume ingredient, correlated with the octanol/water partitioning coefficient thereof, P. Higher P values are more hydrophobic, and since the partitioning coefficients are normally high values, they are conventionally ally referred to in the form of their logarithm to the base 10, or log P. The log P values of many perfume ingredients are readily available from such sources as the Pomona 92 database, available from Daylight Chemical Information Systems, Inc. (Daylight CIS), Irvine, Calif.

However, the log P values are most conveniently calculated by the use of the "C log P" program, also available from Daylight CIS. The "calculated log P" (C log P) is based upon the fragment approach of Hansch and Leo (A. Leo, in *Comprehensive Medicinal Chemistry*, Vol. 4, C. Hansch, P. G. Sammens, J. B. Taylor, and C. A. Ramsden, Eds., p.295, Pergamon Press, 1990, incorporated herein by reference). The C log P values are considered the most reliable and widely used estimates for this important property, and are used instead of experimental log P values in evaluation of hydrophobicity of fragrance ingredients.

It has now been found that such fragrances may be utilized in the presence of a specific surfactant, or a combination of surfactants of the same or differing classes of surfactants, which act as a solubilizer for fragrances having a C log P value greater than about 3, in combination with a specific class of compounds normally referred to as solvents, but which in the present application act as a wetting agent and drying aid. Accordingly, the term surfactant/solubilizer, as used hereinafter, shall be meant to refer to individual surfactants, combinations of surfactants from the same class (ionic, non-ionic, cationic, or amphoteric), and combinations of surfactants from different classes, which have the ability to solubilize perfumes having a C log P higher than about 3. Suitable surfactant/solubilizers for the present invention have been found to include such surfactants as $C_{9-11}$ linear primary alcohol ethoxylates. Other suitable surfactant/solubilizers for use in the present invention include such non-ionics as ethoxylated fatty alcohols, $C_{9-11}$ linear primary alcohols, polyoxyethylene oleyl ethers, and alkoxylated biodegradable hydrotropes; such anionics as ether sulfates and linear ethylene oxide; selected cationics such as quaternary ammonium halides; and selected amphoterics including betaines such as capryloamidopropyl betaine. Thus, the surfactant/solubilizer may preferably be selected from the group consisting of linear primary alcohols, ethoxylated fatty alcohols, linear primary alcohol ethoxylates, polyoxyethylene ethers, alkoxylated biodegradable hydrotropes, linear ethylene oxide, quaternary ammonium halides, betaines, amine oxides, and mixtures thereof. Such surfactant/solubilizers may be used individually or in combination, based upon the solubility parameters of the fragrance to be employed, and may be present in concentrations of from about 0.1 to about 10.0 weight percent and preferably from about 0.5 to 5 weight percent. In the most preferred embodiments of the invention, a $C_{9-11}$ linear primary alcohol ethoxylate surfactant was employed in a concentration of from 1 to 2 percent by weight.

However, it has been found that when a sufficient quantity of the surfactant/solubilizer is employed to ensure dissolution of the fragrance oil, the surfactant/solubilizer frequently leaves a residue, or stain, upon drying. Accordingly, it is desirable to employ an additional solvent material to aid in solubilizing the fragrance, and to help to wet the fabric to which the solution is applied. Since this solvent also acts to enhance drying of the solution, it shall be referred to hereinafter as a solvent/drying aid. Suitable compositions for this purpose include certain water soluble non-VOC solvents, such as butyl carbitol, a diethylene glycol butyl ether. It has been found that both carbitol and butyl carbitol are suitable, and that while butyl carbitol may be preferable for environmental reasons, mixtures of both may be particularly useful. Such solvent drying aids include such compounds as glycol ethers such as ethylene glycol butyl ether, tri(propylene glycol)methyl ether, 1-methoxy-2-propanol, diethylene glycol monoethyl ether, and glycol ether acetates such as propylene glycol methyl ether acetate, and may be present in concentrations of from about 0.05 to about 20 weight percent. In a preferred embodiment of the invention, butyl carbitol was present in a concentration of 4.5 weight percent. Preferred ranges for the solvent/drying aids may range from 1 to about 10 weight percent, more preferably from about 3 to 6 weight percent of the composition, and most preferably from about 4 to 5 weight percent of the composition.

In addition, from about 0.05 to about 5.0 weight percent of an odor absorbing metal salt should be present, selected from the group consisting of water soluble salts of metals such as zinc, copper, silver, zirconium, nickel, chromium and other transition metals. Such salts may include those acetates, chlorides, sulfates, nitrates, gluconates, maleates, lactates, salicylates, and other salts as are water soluble and have odor absorption characteristics. Thus, suitable odor control agents may comprise from 0.05 to about 5.0 weight percent, and preferably from about 0.075 to about 0.2 weight percent (based upon the total weight of the composition) of a water soluble salt selected from the group consisting of the acetates, chlorides, sulfates, nitrates, gluconates, maleates, lactates, and salicylates of zinc, copper, silver, titanium, zirconium, nickel, chromium, and other transition metals.

In addition to the above, it has been found highly beneficial to include in the composition a pH buffering agent, preferably sodium citrate, which may be used in combination with a buffering acid to combat pH drift which occurs upon heating of an aqueous solution of the above noted components. The purpose of a buffering agent is to permit a solution to resist changes in concentration of $H^+$ ions in solution, due to either internal or external influences, such as heating, which may be encountered during storage and shipment of commercial product. Buffers are conventionally composed of weak acids and bases, which do not completely ionize in solution. A combination of sodium citrate and citric acid is the preferred buffering agent for the present invention, due to the presence of three carbonyl groups, resulting in three different $pK_a$ values. Metal salt odor control agents, such as zinc salts, are difficult to stabilize, since zinc ions, for example, tend to form insoluble salts in solution, which may result in a shift in pH, which may result in discoloration or corrosion. Accordingly, it was desired that a buffer system with a pKa value within 1 unit of the desired pH range of 4.5 to 5.5 be selected. It was found that the combination of sodium citrate with citric acid controlled the pH, by serving as a ligand and complexing with the metal from the odor controlling metal salt, to form a chelate which tied up the chemical reactivity, but not the odor complexing capabilities of the metal ions. The target pH for the present invention is in the range of from about 4.5 to about 5.5, while the effective $pK_a$ values for citric acid in such a solution are from about 4.7 to about 5.4, creating an effective system to control the formula pH in the target range. While sodium citrate is the preferred citrate, other citrates, such as potassium citrate, are also suitable. Other acids in the appropriate pKa range may also be used in place of citric acid, such as succinic and acetic acids. Appropriate amounts of buffering agent, comprising a citrate salt in combination with a buffering acid, should be added to achieve the desired pH. Buffering acid may be added in addition, to arrive at the appropriate target pH range. It is also to be noted that a buffering acid may not be required if the surfactant itself is acidic and can thus serve as an ion donor.

Still further, optional components may be included, such as from 0 to about 1.0 weight percent of a preservative or stabilizer; from 0 to about 10.0 weight percent of a moth or insect repellant; from 0 to about 10 weight percent anti-static compound; from 0 to about 5 weight percent of an antimicrobial compound; and from 0 to about 0.5 weight percent of a coloring agent. Other suitable optional components may be added, as will be apparent to those skilled in the art, without detracting from the efficacy of the presently set forth compositions, and such shall be considered within the scope of the present invention.

As indicated, a preservative may also be present, although not required for the purpose of the present invention. Suitable preservatives are well known in the art, and include such compositions as Kathon® CG, a 5-Chloro-2-methyl-4-isothiazolin-3one compound available from Rohm & Haas. The concentration of preservative should be sufficient to perform the function for which it is added, and may be, for example, 0.05 weight percent of the composition. The preservative may be any organic preservative material which will not cause damage to the surfaces to which the solutions are to be applied, such as discoloration, coloration, or bleaching. Preferred water soluble preservatives include organic sulfur compounds, halogenated compounds, cyclic organic nitrogen compounds, low molecular weight aldehydes, quaternary compounds, dihydroacetic acid, phenyl and phenoxy compounds, and mixtures thereof.

In addition, antimicrobial or antibacterial compositions may also be present, although not required in the present invention. Suitable compounds for this purpose include such compounds as Myristalkonium chloride and Quatemium 14. Other well known water soluble antimicrobial agents may be used, such as Benzylkonium chloride, zinc gluconate, antimicrobial anionic surfactants, and quatemary amphoteric surfactants.

Still further, other compositions may be present for specific purposes, such as anti-static, and anti-wrinkling additives. Suitable compositions for these purposes include monoalkyl cationic quatemary ammonium compounds, polyethylene glycols, polymeric quaternary ammonium salts, quaternized polyethyleneimines, etc, Other textile treatment agents like water-proofing, flame retardants, UV protectants or stain repellents may also be appropriate.

Insect control or moth repelling agents may also be optionally included, such as pheromones, citronellol, citranellal, citral, linalool, etc. Many such compositions are known in the art, and the specific agents employed are a matter of choice, dependent upon the specific need of the consumer.

The aqueous solutions of the present invention may be utilized in a variety of ways. The most commonly employed method for application of malodor counteractants is to spray the composition on the surface of the fabric, clothing, furniture, or other object which is subject to the presence of the unpleasant odor, spraying sufficient solution to slightly dampen the surface. This is most easily accomplished by means of a spray bottle, comprising a container, most favorably a light weight flexible plastic, and a spray nozzle means by which the liquid may be forced, under pressure provided by either a pump mechanism or by pressurization of the container. Such a spray application of the solution of the present invention is accordingly considered within the scope of the invention, as is the means thereof including both liquid spray, as above, and aerosol application. In addition, it is possible that the solution of the present invention may be applied by alternative means, such as by addition to a rinse cycle during laundering or dry-cleaning, or by direct application of the liquid solution to the surface by pouring, rubbing with a liquid containing absorbent material, etc. Preferably, the amount of solution applied need not saturate or cause a pooling of liquid on the article or surface, but should be sufficient to achieve the elimination or decrease of malodor without leaving a readily discernible visible deposit after drying.

EXAMPLES

A number of test materials were mixed and evaluated for clarity and residue remaining on a fabric sample after drying. These results are shown in Tables 1A and 1B. The test samples in each instance in Table 1A contained 4 weight percent diethylene glycol monoethyl ether as a solvent/drying aid, and 0.3 weight percent of fragrance. The first group of surfactant/solubilizers were subjected to a general screening test to determine whether an acceptable residue level could be achieved. These four samples were adjusted to the appropriate pH range with citric acid alone, with no sodium citrate. The remaining examples, using the $C_{9-11}$ ethoxylate surfactant/solubilizer, all had a pH buffer, comprising both citric acid and sodium citrate, present.

In Table 1B, the results of a screening test of possible solvent/dryers is shown. In these examples, the tested solvent/dryers were evaluated in solution with 2 weight percent of $C_{9-11}$ linear primary alcohol ethoxylate surfactant/solubilizer, 0.3 percent fragrance, sufficient buffering agent to maintain the desired pH, and a zinc salt deodorizer.

In addition to optimizing the formulations containing both ethylene glycol butyl ether and $C_{9-11}$ linear primary alcohol ethoxylate, additional glycol ethers were evaluated. Results of these experiments are shown in Table 2.

TABLE 1A

| Surfactant/solubilizer | Class | % | pH | Clarity | Residue |
| --- | --- | --- | --- | --- | --- |
| capryloamidopropyl betaine | ampho-teric | 2.00 | 5.67 | milky | not sprayed |
| Cetyl betaine | ampho-teric | 2.00 | 4.57 | clear | none |
| Sodium lauryl sarcosinate, 30% | anionic | 2.00 | 7.25 | hazy | none |
| Ammonium laureth sulfate EA2 | anionic | 2.00 | 4.73 | milky | none |
| Sodium lauryl sulfate | anionic | 2.00 | 4.12 | milky | none |
| Cocamidopropyl amine oxide | nonionic | 2.00 | 5.26 | clear | none |

TABLE 1A-continued

| Surfactant/solubilizer | Class | % | pH | Clarity | Residue |
|---|---|---|---|---|---|
| C9–11 linear primary alcohol ethoxylate | nonionic | 0.30 | 5.27 | cloudy | not sprayed |
| C9–11 linear primary alcohol ethoxylate | nonionic | 0.60 | 5.26 | cloudy | not sprayed |
| C9–11 linear primary alcohol ethoxylate | nonionic | 0.90 | 5.21 | hazy | not sprayed |
| C9–11 linear primary alcohol ethoxylate | nonionic | 1.20 | 5.21 | clear | not sprayed |
| C9–11 linear primary alcohol ethoxylate | nonionic | 1.50 | 5.23 | clear | not sprayed |
| C9–11 linear primary alcohol ethoxylate | nonionic | 1.80 | 5.21 | clear | not sprayed |
| C9–11 linear primary alcohol ethoxylate | nonionic | 5.00 | 5.46 | clear | visible |
| C9–11 linear primary alcohol ethoxylate | nonionic | 7.00 | 5.47 | clear | visible |

TABLE 1B

| Solvent/dryer | Type | % | pH | Clarity | Residue |
|---|---|---|---|---|---|
| tri(propylene glycol) methyl ether | glycol ether | 4.00 | 4.85 | clear | none |
| ethylene glycol butyl ether | glycol ether | 4.00 | 5.26 | clear | visible |
| 1-methoxy-2-propanol | glycol ether | 4.00 | 4.97 | clear | visible |
| Diethylene glycol butyl ether | glycol ether | 0.00 | 5.28 | clear | visible |
| Diethylene glycol butyl ether | glycol ether | 1.00 | 5.03 | clear | visible |
| Diethylene glycol butyl ether | glycol ether | 2.00 | 5.17 | clear | slightly visible |
| Diethylene glycol butyl ether | glycol ether | 0.50 | 5.32 | clear | visible |
| Diethylene glycol butyl ether | glycol ether | 1.50 | 5.33 | clear | visible |
| Diethylene glycol butyl ether | glycol ether | 10.00 | 5.48 | clear | none |
| Diethylene glycol monoethyl ether | glycol ether | 1.00 | 5.48 | clear | visible |
| Diethylene glycol monoethyl ether | glycol ether | 2.00 | 5.12 | clear | visible |
| Diethylene glycol monoethyl ether | glycol ether | 0.50 | 5.31 | clear | visible |
| Diethylene glycol monoethyl ether | glycol ether | 1.50 | 5.21 | clear | visible |

TABLE 2

| Raw material | 190-1 | 190-2 | 190-3 | 190-4 | 190-5 | 190-6 | 191-1 | 191-2 | 191-3 | 191-4 |
|---|---|---|---|---|---|---|---|---|---|---|
| Diethylene glycol butyl ether | 2.500 | 3.000 | 2.500 | 2.500 | 3.000 | 2.500 | 3.000 | 0.000 | 0.000 | 2.750 |
| Tri(propylene glycol) methyl ether | 0.000 | 0.000 | 0.000 | 0.000 | 0.000 | 0.000 | 0.000 | 2.500 | 2.500 | 0.000 |
| C9–11 linear primary alcohol ethoxylate | 1.000 | 1.000 | 1.100 | 1.200 | 1.200 | 1.500 | 1.500 | 1.200 | 1.500 | 1.500 |
| Zinc sulfate heptahydrate | 0.110 | 0.110 | 0.110 | 0.110 | 0.110 | 0.110 | 0.110 | 0.110 | 0.110 | 0.110 |
| Sodium citrate | 0.150 | 0.150 | 0.150 | 0.150 | 0.150 | 0.150 | 0.150 | 0.150 | 0.150 | 0.150 |
| Citric acid (50%) | 0.026 | 0.026 | 0.026 | 0.026 | 0.026 | 0.026 | 0.026 | 0.026 | 0.026 | 0.026 |
| Myristalkonium chloride and Quaternarium 14 antimicrobials | 0.430 | 0.430 | 0.430 | 0.430 | 0.430 | 0.430 | 0.430 | 0.430 | 0.430 | 0.430 |
| Fresh floral fragrance | 0.300 | 0.300 | 0.300 | 0.300 | 0.300 | 0.300 | 0.300 | 0.300 | 0.300 | 0.300 |
| Distilled water | qs | qs | qs | qs | qs | qs | qs | qs | qs | qs |
| TOTAL | 100.00 | 100.00 | 100.00 | 100.00 | 100.00 | 100.00 | 100.00 | 100.00 | 100.00 | 100.00 |
| pH | 5.14 | 5.17 | 5.11 | 5.22 | 5.18 | 5.04 | 5.17 | 5.14 | 5.21 | 5.17 |
| Appearance of solution | clear | clear | clear | clear | clear | clear | clear | clear | clear | clear |
| Appearance of solution after | | | | | | | | | | |
| 24 hours at room temperature | clear | clear | clear | clear | clear | clear | clear | clear | clear | clear |
| 24 hours at 50° F. | | | | | hazy | hazy | clear | hazy | clear | clear |
| 24 hours at 100° F. | clear | clear | clear | clear | clear | clear | clear | clear | clear | clear |

TABLE 3

| Raw material | Formula 1 Weight % | Formula 2 Weight % | Formula 3 Weight % | Formula 4 Weight % | Formula 5 Weight % |
|---|---|---|---|---|---|
| Diethylene glycol monethyl ether | 4.0 | 4.0 | | | 4.0 |
| Diethylene glycol butyl ether | | | 4.5 | 3.0 | |
| Polyoxyethylene (10) oleyl ether | 0.4 | 0.5 | | | |
| Alkoxylated biodegradable hydrotrope | | 0.5 | | | |
| Ethoxylated straight chain alcohol | 0.4 | | | | |
| C9–11 linear primary alcohol | | | 2.0 | 1.0 | 2.0 |
| Fresh Clean Fragrance 1 | 0.3 | | | | |
| Fresh Clean Fragrance 2 | | 0.25 | 0.3 | 0.3 | |
| Heavy Floral Fragrance | | | | | 0.25 |
| 25% Zinc acetate solution | 0.3035 | 0.2276 | | | 0.2276 |
| Zinc sulfate heptahydrate | | | 0.11 | 0.11 | |
| Methyl-isothiazolone & chloromethyl isothiazolone | 0.05 | 0.05 | | | |
| 1,2 Ethanediylbis (oxy)-bis-methanol | | | | | 0.05 |
| Sodium citrate, USP, dihydrate | 0.1 | 0.1 | 0.15 | 0.15 | 0.1 |
| Citric acid, 50% solution | | | 0.026 | 0.026 | |

TABLE 3-continued

| Formulas<br>Raw material | Formula 1<br>Weight % | Formula 2<br>Weight % | Formula 3<br>Weight % | Formula 4<br>Weight % | Formula 5<br>Weight % |
| --- | --- | --- | --- | --- | --- |
| Acetic acid, 30% | 0.05 | 0.05 | | | |
| Acetic acid, 80% | | | | | 0.0188 |
| Myristalkonium chloride | | | 0.1075 | 0.1075 | |
| Quaternium 14 | | | 0.1075 | 0.1075 | |
| Deionized water | q.s. | q.s. | q.s. | q.s. | q.s. |

After these experiments, various fragrances, including fresh clean, heavy floral, and fresh clean 2, all having a C log P greater than 3, were tested with a preferred combination of butyl carbitol and carbitol with $C_{9-11}$ linear primary alcohol ethoxylate, and found to be soluble. These dissolved fragrances were then sprayed on fabrics, and found to leave little or no residue, to dry relatively quickly, and to leave a pleasant impression.

INDUSTRIAL APPLICABILITY

The present invention provides a readily produced combination of materials, using chemicals and compositions which are commonly available for the freshening of various fabrics and other surfaces and removal of malodors. Further, the surface treatment compositions provided present a positive improvement over those compositions presently employed for the same purposes. The methods of preparation and application of the solutions of the present invention are readily achievable by one is skilled in the art.

While the present invention has been described with respect to what are at present considered to be the preferred embodiments, it is to be understood that the invention is not to be limited to the disclosed embodiments. To the contrary, the invention is intended to cover various modifications and equivalent arrangements within the spirit and scope of the appended claims. The scope of the following claims is to be accorded the broadest interpretation so as to encompass all such modifications and equivalent formulations and functions.

What is claimed is:

1. An aqueous composition for reducing malodor impression, said composition containing no volatile organic compounds and comprising:
   a. from about 0.01 to about 1.0 weight percent of a hydrophobic fragrance selected from the group consisting of fresh clean, spicy, floral, citrus, ozone, and marine type perfumes;
   b. from about 0.01 to 10.0 weight percent of a non-volatile organic compound surfactant/solubilizer selected from the group consisting of nonionic, anionic, cationic, and amphoteric surfactants having the ability to solubilize perfumes having a C log P value greater than about 3, wherein said surfactant/solubilizer is selected from the group consisting of linear primary alcohol ethoxylates, ethoxylated fatty alcohols, linear primary alcohols, polyoxyethylene ethers, alkoxylated biodegradable hydrophobes, linear ethylene oxide, quaternary ammonium halides, ether sulfates, betaines, amine oxides, and mixtures thereof;
   c. from about 0.01 to about 20.0 weight percent of a water soluble non-volatile organic compound solvent/drying aid for said fragrance, wherein said drying aid is selected from the group consisting of glycol ethers, glycol ether acetates, and mixtures thereof;
   d. from about 0.05 to about 5.0 weight percent odor absorber comprising a water soluble salt of a metal selected from the group consisting of zinc, copper, silver, zirconium, nickel, chromium, and other transition metals;
   e. sufficient buffering agent to maintain the pH of the solution between 3 and 7, said agent comprising a mixture of sodium citrate and a buffering acid present in sufficient quantity to maintain said solution at a pH level between 4.5 and 5.5; and
   f. the balance water.

2. The aqueous composition of claim 1, wherein said non-volatile organic compound solvent/drying aid is selected from the group consisting of glycol ethers, glycol ether acetates, and mixtures thereof.

3. The aqueous composition of claim 1, wherein said surfactant/solubilizer is a linear primary alcohol ethoxylate, comprising from about 1 to about 2 weight percent of the composition.

4. The aqueous composition of claim 3, wherein said solvent/drying aid is a glycol ether, comprising from about 3 to about 6 weight percent of said composition.

5. The composition of claim 4, wherein said solvent/drying aid is selected from the group consisting of diethylene glycol monoethyl ether, diethylene glycol butyl ether, and mixtures thereof, and comprises from about 4 to about 5 weight percent of the composition.

6. The composition of claim 3, wherein said odor absorber is a water soluble zinc salt, comprising from about 0.075 to about 0.2 weight percent of the composition.

7. An aqueous composition having a pH between about 3 and about 7, said composition containing no volatile organic compounds and comprising:
   a. from about 0.01 to about 1.0 percent of a perfume having a C log P value greater than about 3, said perfume selected from the group consisting of fresh clean, spicy, floral, citrus, ozone, and marine type perfumes;
   b. from about 0.01 to about 10 percent of a surfactant/solubilizer for said perfume selected from the group consisting of linear primary alcohols, ethoxylated fatty alcohols, linear primary alcohol ethoxylates, polyoxyethylene ethers, alkoxylated biodegradable hydrotropes, ether sulfates, linear ethylene oxide, quaternary ammonium halides, betaines, amine oxides, and mixtures thereof;
   c. from about 0.01 to about 20 percent of a solvent/drying aid for said perfume selected from the group consisting of glycol ethers, glycol ether acetates, and mixtures thereof; and
   d. from about 0.01 to about 10 percent of an odor absorber selected from the group consisting of water soluble salts of a metal selected from the group consisting of zinc, copper, silver, zirconium, nickel, and chromium.

8. The aqueous composition of claim 7, further comprising one or more further components selected from the group consisting of preservatives, antimicrobials, anti-static compositions, anti-wrinkling agents, insect control agents, moth repellents, UV protectants, waterproofing agents, color protectants, and other textile treatment agents.

9. The aqueous composition of claim 8, wherein said surfactant/solubilizer is a linear primary alcohol ethoxylate comprising from about 0.5 to about 5 percent of the composition.

10. The aqueous composition of claim 8, wherein said solvent/drying aid is selected from the group consisting of glycol ethers and mixtures thereof, and comprises from about 1 to about 10 percent of the composition.

11. The aqueous composition of claim 10, wherein said solvent/dying aid comprises a mixture of diethylene glycol monoethyl ether and diethylene glycol butyl ether, and comprises from about 3 to about 6 percent of the composition.

12. The aqueous composition of claim 8, wherein said odor absorber is a zinc salt.

13. A method for reducing malodor of a surface, said method comprising applying to said surface an effective amount of an aqueous solution containing less than about 0.25 weight percent of volatile organic compounds and comprising a hydrophobic perfume selected from the group consisting of fresh clean, spicy, floral, citrus, ozone, and marine type perfumes; a non-volatile organic compound surfactant/solubilizer for said perfume selected from the group consisting of linear primary alcohols, ethoxylated fatty alcohols, linear primary alcohol ethoxylates, polyoxyethylene ethers, alkoxylated biodegradable hydrotropes, ether sulfates, linear-ethylene oxide, quaternary ammonium halides, betaines, amine oxides, and mixtures thereof; a non-volatile organic compound solvent/drying aid for said perfume selected from the group consisting of glycol ethers, glycol ether acetates, and mixtures thereof; a water soluble metal salt odor absorber selected from the group consisting of water soluble salts of a metal selected from the group consisting of zinc, copper, silver, zirconium, nickel, and chromium; and sufficient buffering agent comprising a citrate salt, provided that when said surfactant/solubilizer is not acidic, said buffering agent further comprises an acid selected from the group consisting of citric, succinic, and acetic acids, to maintain the pH of said composition between about 3 and about 7; and permitting said surface to dry.

14. The method of claim 13, wherein said surfactant/solubilizer is a linear primary alcohol ethoxylate comprising 0.5 to about 5 percent of the composition.

15. The method of claim 13, wherein said solvent/drying aid is selected from the group consisting of glycol ethers and mixtures thereof, and comprises from about 1 to about 10 percent of the composition.

16. The method of claim 15, wherein said solvent/drying aid is a mixture of diethylene glycol monoethyl ether and diethylene glycol butyl ether, and comprises from about 4 to about 5 percent of the composition.

17. The method of claim 13, wherein said surfactant/solubilizer comprises from about 0.5 to about 5 percent of a linear primary alcohol ethoxylate; said solvent/drying aid comprises from about 4 to about 5 percent of a mixture of diethylene glycol monoethyl ether and diethylene glycol butyl ether; said odor absorber comprises from 0.01 to 10 percent of a zinc salt; and said composition has a pH between 4.5 and 5.5.

* * * * *